US007182754B2

(12) United States Patent
Brigham et al.

(10) Patent No.: US 7,182,754 B2
(45) Date of Patent: Feb. 27, 2007

(54) CONTAINERLESS TISSUE SAMPLE COLLECTION TRAP

(75) Inventors: Lynette E. Brigham, West Roxbury, MA (US); Nathaniel M. Beale, Harvard, MA (US); Stephen D. Feid, Plainville, MA (US)

(73) Assignee: N.M. Beale Company, Harvard, MA (US)

( * ) Notice: Subject to any disclaimer, the term of this patent is extended or adjusted under 35 U.S.C. 154(b) by 278 days.

(21) Appl. No.: 10/174,854

(22) Filed: Jun. 19, 2002

(65) Prior Publication Data

US 2003/0236507 A1    Dec. 25, 2003

(51) Int. Cl.
| | |
|---|---|
| *B01D 29/00* | (2006.01) |
| *B01D 39/10* | (2006.01) |
| *A61B 10/00* | (2006.01) |
| *A61B 5/00* | (2006.01) |
| *A61M 1/00* | (2006.01) |
| *A61M 31/00* | (2006.01) |

(52) U.S. Cl. ............... 604/317; 210/499; 210/348; 210/497.01; 604/276; 604/326; 600/562; 600/573

(58) Field of Classification Search ............ 604/6.09, 604/190, 276, 317, 319, 326; 210/348, 464, 210/497.01, 497.2, 497.3, 499, 435; 600/101, 600/562–584, 533–539
See application file for complete search history.

(56) References Cited

U.S. PATENT DOCUMENTS

| | | | | |
|---|---|---|---|---|
| 872,437 | A * | 12/1907 | Leonard | 210/409 |
| 1,832,776 | A * | 11/1931 | Hudson | 210/94 |
| 2,936,099 | A * | 5/1960 | Smith | 222/189.06 |
| 2,982,418 | A * | 5/1961 | Ronald | 210/448 |
| 3,224,434 | A * | 12/1965 | Molomut et al. | 600/562 |
| 3,623,483 | A * | 11/1971 | Dyer, Jr. | 604/266 |
| 3,817,389 | A * | 6/1974 | Weichselbaum | 210/448 |
| 3,889,657 | A * | 6/1975 | Baumgarten | 600/571 |
| 3,890,712 | A * | 6/1975 | Lopez | 433/92 |
| 3,933,652 | A * | 1/1976 | Weichselbaum et al. | 210/446 |
| 3,976,529 | A * | 8/1976 | Weichselbaum | 156/272.4 |
| 4,014,797 | A * | 3/1977 | Raines et al. | 210/446 |
| 4,083,706 | A * | 4/1978 | Wiley | 55/385.1 |
| 4,387,725 | A * | 6/1983 | Mull | 600/572 |
| 4,413,675 | A * | 11/1983 | Gano | 165/119 |
| 4,643,197 | A | 2/1987 | Greene et al. | |
| 4,813,931 | A * | 3/1989 | Hauze | 604/540 |
| 5,035,688 | A * | 7/1991 | Inui | 604/190 |
| 5,108,381 | A | 4/1992 | Kolozsi | |
| 5,281,331 | A * | 1/1994 | Golan | 210/131 |
| 5,354,468 | A * | 10/1994 | Richards | 210/448 |
| 5,393,496 | A * | 2/1995 | Seymour | 422/101 |
| 5,492,413 | A * | 2/1996 | Tsukada | 384/15 |
| 5,630,939 | A * | 5/1997 | Bulard et al. | 210/416.1 |

(Continued)

*Primary Examiner*—Tatyana Zalukaeva
*Assistant Examiner*—Michael G. Bogart
(74) *Attorney, Agent, or Firm*—Iandiorio & Teska (57) ABSTRACT

A containerless tissue sample collection trap featuring, in the preferred embodiment, a flexible filter and an applicator having a shaft terminating in a distal end with a channel therein receiving a portion of the flexible filter, the combination of the applicator and the flexible filter receivable in a suction tube and configured such that when the applicator is removed, the flexible filter forms a removable elongated tissue trap in the suction tube. Also disclosed is a method of trapping tissue wholly within a suction tube thereby eliminating the need for a specimen trap container and a method of making a containerless tissue specimen trap.

45 Claims, 11 Drawing Sheets

U.S. PATENT DOCUMENTS

| | | | |
|---|---|---|---|
| 5,766,134 A * | 6/1998 | Lisak et al. | 600/562 |
| 5,779,649 A * | 7/1998 | Herbert | 600/571 |
| 6,176,093 B1 * | 1/2001 | Stein et al. | 62/85 |
| 6,183,254 B1 * | 2/2001 | Cohen | 433/92 |
| 6,299,763 B1 * | 10/2001 | Ashman | 210/94 |
| 6,368,309 B1 * | 4/2002 | Yeh | 604/315 |
| 6,428,316 B1 * | 8/2002 | Rodriquez | 433/92 |
| 6,481,301 B2 * | 11/2002 | Pawliszyn | 73/864.71 |
| 6,539,817 B2 * | 4/2003 | Kozak et al. | 73/864.91 |
| 6,695,791 B2 * | 2/2004 | Gonzalez | 600/562 |
| 6,872,184 B2 * | 3/2005 | Brannon | 600/562 |

* cited by examiner

CONTAINERLESS TISSUE SAMPLE COLLECTION TRAP

FIELD OF THE INVENTION

This invention relates to a method of trapping tissue wholly within a suction tube or conduit thereby eliminating the need for a separate tissue specimen trap container. This invention also relates to a containerless tissue sample collection trap.

BACKGROUND OF THE INVENTION

Tissue sample collection and drainage traps are known in the art. See for example U.S. Pat. Nos. 4,643,197 and 5,108,381 incorporated herein by this reference.

Typically, an endoscope is used in combination with a biopic surgical instrument whereby tissue specimens along with fluid can be extracted under suction from a body cavity and carried through the endoscope into a tissue specimen trap container interconnected between a) the endoscope or a suction tube leading to the endoscope and b) a suction tube leading to a fluid collection container and/or the vacuum source. Polyps are extracted and collected in this manner for biopsy and analysis.

The specimen trap container housing the collected tissue is then disconnected from the endoscope and the suction tube. It is intended by the manufacturer that the specimen trap container be used as the means for transferring the specimen to a pathologist who ultimately examines the collected tissue sample. The truth is, most pathologists direct the hospital technicians and nurses to extract the tissue sample from the specimen trap container and then place the tissue sample in a specimen vial filled with formaldehyde. Once the pathologist receives the specimen vial, the pathologist then removes the tissue sample from the specimen vial and examines it.

Thus, prior art tissue sample collection traps which can range in cost from $2–6 are actually only used for trapping tissue and they are then discarded. Several designs have attempted to solve the problem of extracting the tissue sample from the fluid within the trap and, for example, have added filters with a number of individual tissue traps (see the '197 patent) but such designs are unduly complex and thus even more expensive.

Moreover, the traps themselves must be discarded in biohazard containers which increases the cost to the hospital and ultimately to the patient.

SUMMARY OF THE INVENTION

It is therefore an object of this invention to provide a new tissue sample collection trap.

It is a further object of this invention to provide a method of trapping tissue wholly within a suction tube thereby eliminating the need for a separate tissue specimen trap container.

It thus an object of this invention to provide a tissue sample collection trap which has no container.

It is a further object of this invention to provide such a containerless tissue sample collection trap which is small in size thus saving inventory resulting in lower inventory costs.

It is a further object of this invention to provide such a containerless tissue sample collection trap which is small in size and which thus reduces disposal costs.

It is a further object of this invention to provide a method of trapping tissue wholly within a suction tube and in which only tissue is trapped—not any fluid—thus providing an easier and less messy tissue collection method.

It is a further object of this invention to provide a containerless tissue sample collection trap which can be manufactured at much lower cost thus resulting in cost savings to the hospital and the patient.

It is a further object of this invention to provide a tissue sample collection trap which itself can be placed directly in a specimen vial for later pathological examination.

It is a further object of this invention to provide a tissue sample collection trap which is easy for the pathologist to remove from the specimen vial.

The invention results from the realization that a less complex tissue trap which traps no fluid and is easier to use is effected in a containerless design and wherein the suction tube itself serves as the tissue collection "container" and a piece of flexible filter material such as netting is disposed within the suction tube preferably using a special applicator pre-loaded with the netting.

This invention features a containerless tissue sample collection trap comprising a flexible filter and an applicator having a shaft terminating in a distal end with a channel therein receiving a portion of the flexible filter, the combination of the applicator and the flexible filter receivable in a suction tube and configured such that when the applicator is removed, the flexible filter forms a removable elongated tissue trap in the suction tube.

Typically, the flexible filter is made of a single ply of plastic netting between 2 and 5 inches in diameter having pores between 0.01 and 0.05 inches in perimeter and between 1,000 and 2,000 pores per square inch.

In the preferred embodiment, the applicator is also made of plastic and has a broad proximal end opposite the distal end for easier insertion of the distal end thereof into the suction tube. Also, the distal end of the applicator is typically flat and the channel extends through the flat distal end and continues within the shaft. In one example, the outer diameter of the distal end is between 0.4 and 0.5 inches, the inner diameter of the distal end is between 0.1 and 0.2 inches, the shaft is between 1 and 2 inches in length, and the channel is between 0.7 and 0.8 inches in length.

This invention is not limited to the example above, however. Thus, the containerless tissue sample collection trap of this invention features filter means for trapping a tissue sample within a suction tube and applicator means for removably inserting the filter means in the suction tube, the applicator means removable from the suction tube and separable from the filter means after the filter means is inserted in the suction tube. In the preferred embodiment, the applicator means includes a channel therein for receiving a portion of the filter means which is disposed in the suction tube after the applicator means is removed therefrom.

The tissue collection trap of this invention may include a filter for trapping a tissue sample within a suction tube and an applicator for removably inserting at least a portion of the filter in the suction tube.

A containerless tissue sample collection trap in accordance with this invention features a flexible filter and an applicator having a shaft terminating in a distal end for urging at least a portion of the flexible filter into a suction tube, the combination of the applicator and the flexible filter receivable in a suction tube and configured such that the flexible filter thereby forms a removable elongated tissue trap in the suction tube. In the preferred embodiment, the applicator has a channel therein extending from the distal end thereof and a portion of the flexible filter is received therein.

This invention also features a method of trapping tissue wholly within a suction tube thereby eliminating the need for a tissue specimen trap container. The method comprises loading at least a portion of a flexible filter onto an applicator, disconnecting one end of a suction tube, urging the applicator and the flexible filter into the disconnected end of the suction tube, optionally removing the applicator, and reconnecting the end of the suction tube.

The flexible filter is typically disposed at least partially within the applicator. The method may further include the step of disconnecting the suction tube and removing the flexible filter and a tissue sample trapped therein from the suction tube, of placing the flexible filter and the tissue sample trapped therein in a specimen vial, of removing the flexible filter and the tissue sample trapped therein from the specimen vial, and of removing the tissue sample from the flexible filter for examination.

A method of trapping tissue wholly within a suction tube in accordance with this invention may include the steps of disconnecting one end of a suction tube, urging the distal end of an applicator preloaded with a flexible filter into the disconnected end of the suction tube, optionally removing the applicator, and reconnecting the end of the suction tube.

This invention also features a method of making a containerless tissue trap, the method comprising forming an applicator with a shaft terminating in a distal end with a channel therein, and inserting a portion of a flexible filter into the channel, the combination of the applicator and the flexible filter receivable in a suction tube and configured such that when the applicator is removed, the flexible filter forms a removable elongated tissue trap in the suction tube.

A containerless tissue sample collection trap in accordance with this invention may comprise a suction tube and a filter disposed in the suction tube and configured such that the flexible filter forms a removable elongated tissue trap in the suction tube. An applicator is preferably supplied for disposing the filter in the suction tube.

A containerless tissue sample collection trap in accordance with this invention features a first conduit having a fitting on one end thereof, a second conduit having an end section connectable to the fitting of the first conduit forming a junction between the two conduits, the fitting and/or the end section of the second conduit being pliable to join the two conduits, and a filter removably disposed in the end section of the second conduit such that when the first conduit is joined to the second conduit tissue is trapped in the end section of the second conduit.

In one example the fitting on the first conduit is a female fitting received in the end section of the second conduit. In another example, the end section of the second conduit also includes a fitting (e.g., male or female) and the filter is disposed in the fitting. Preferably, the filter is made of a flexible material forming an elongated tissue trap in the second conduit and having material extending out of the joint between the two conduits and an applicator is provided for disposing the filter in the end section of the second conduit.

A method of trapping tissue within a conduit in accordance with this invention features disconnecting a first conduit having a fitting on one end from a second conduit having an end section connected to the fitting of the first conduit, disposing a filter in the end section of the second conduit, and reconnecting the fitting of the first conduit to the end section of the second conduit.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings.

Figure 1:
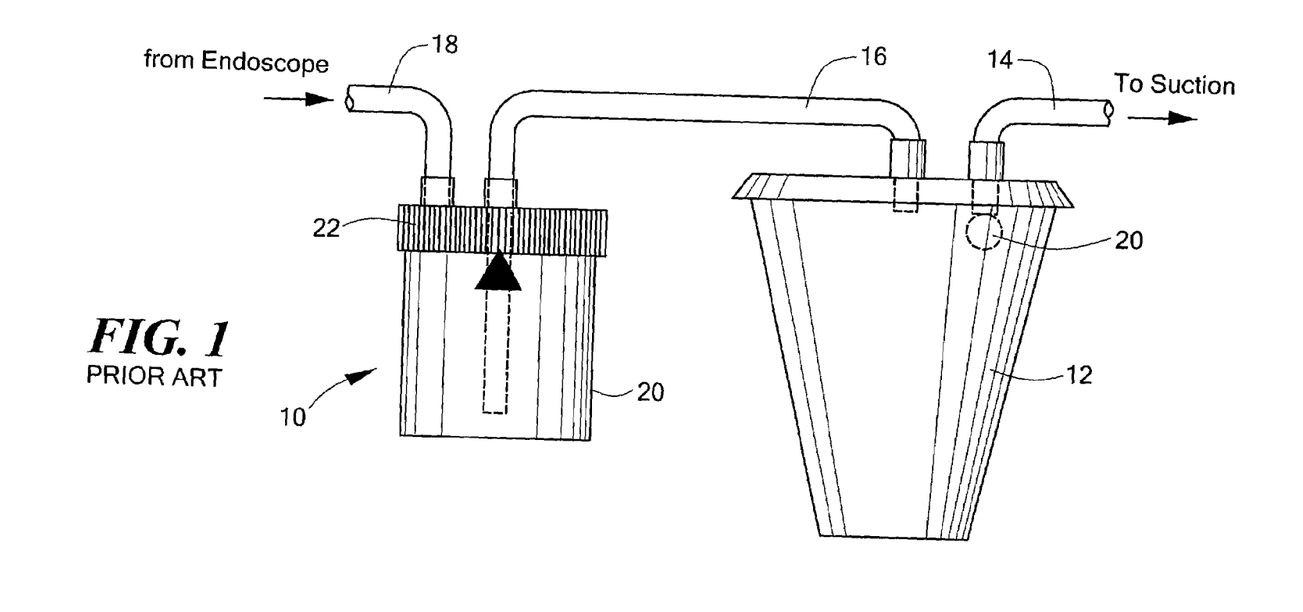
FIG. 1 is a schematic view of a prior art suction collection and drainage apparatus.

Prior art tissue trap 10, FIG. 1 is interconnected between an endoscope and fluid collection container 12 which is connected via suction tube 14 to a vacuum source. Suction tube 16 interconnects fluid collection container 12 and trap 10 and suction tube 18 connects trap 10 with the endoscope. Typical tissue collection traps include container 20, lid 22, tubes 18 and 16 and structure to prevent extracted tissue from escaping out vacuum tube 16, for example, a filter integral with the inside of lid 22 between container 22 and suction tube 16. The endoscope is used to cut tissue from within a body cavity and the tissue travels through the endoscope and suction tube 18 to container 20.

As discussed in the Background section above, typical tissue traps cost between $2–6 and most still collect fluid along with the specimen. So, the nurse or technician must remove lid 22 and extract the tissue sample from within container 20 after vacuum tubes 16 and 18 are disconnected. Tissue trap 10 is then discarded in a biohazard receptacle.

The tissue specimen is then placed in a specimen vial filled with formaldehyde and transported to the pathology lab where the tissue specimen must now be removed from the formaldehyde filled specimen vial for further study.

If container 20, lid 22, and the other structure associated with trap 10 were eliminated, hospitals and other patient care institutions would clearly save inventory and disposal costs.

Figure 2:
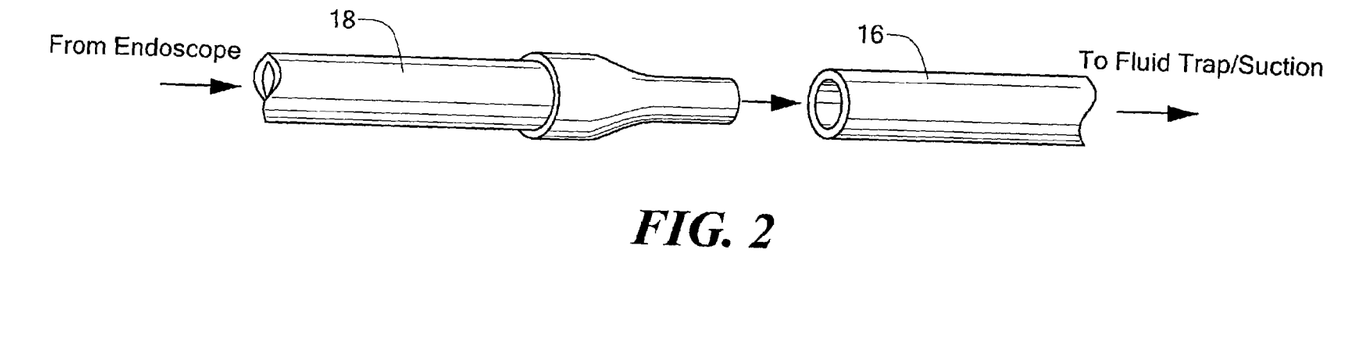
FIG. 2 is a schematic view showing a typical interconnection between an endoscope and a suction tube.
Figure 8:
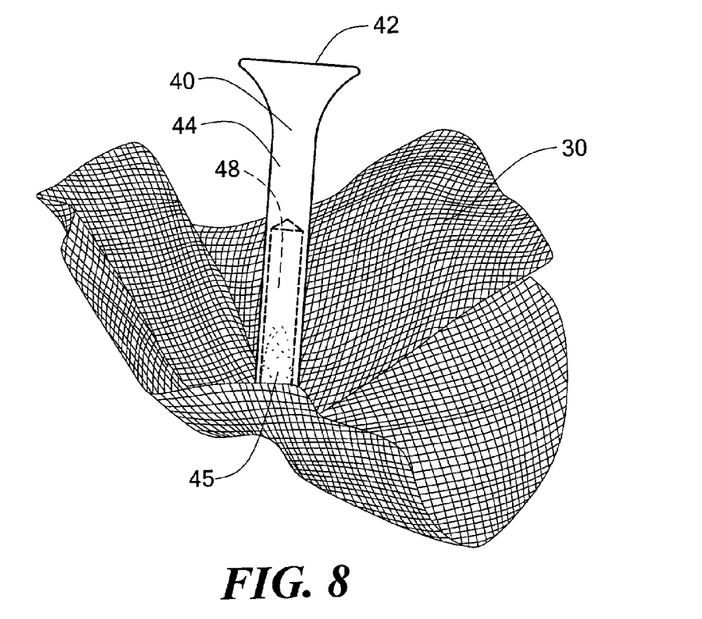
FIG. 8 is a schematic view showing, in one example, a containerless tissue sample collection trap in accordance with the subject invention wherein the flexible filter is preloaded in the applicator.

In this invention, vacuum tube or conduit 16, FIG. 2 is used as the "container" for the tissue trap thus eliminating many of the problems associated with prior art tissue traps. The containerless tissue sample collection trap of this invention features flexible filter 30, FIG. 3, typically a single ply of plastic netting between 2 inches and 5 inches (e.g., 3.75 inches) in diameter. The preferred netting has pores between 0.01 and 0.05 inches in perimeter and there are between 1,000 and 2,000 (e.g., 1,600) pores per square inch. The containerless tissue sample collection trap of this invention also features applicator 40, FIGS. 4–7. In one example, plastic applicator 40 preferably includes broad proximal end 42 (e.g., 0.480 inches in diameter) with shaft 44 extending therefrom terminating in flat distal end 46 with channel 48 therethrough extending up into shaft 44. Channel 48 receives a portion 45 (typically the center portion) of flexible filter 30, FIG. 3 in the "loaded" position as shown in FIG. 8.

Figure 3:
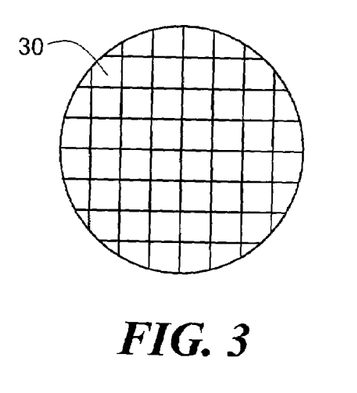
FIG. 3 is a top view of the preferred embodiment of the flexible filter of the subject invention.
Figure 9:
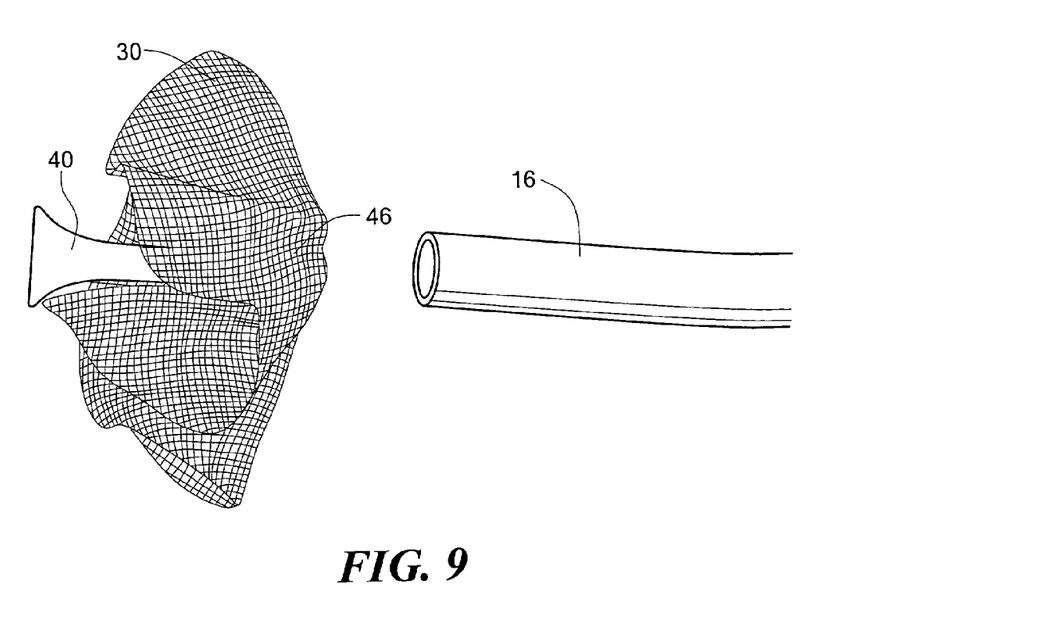
FIG. 9 is a schematic view showing how, in accordance with the method of this invention, the containerless tissue sample collection trap of FIG. 8 is disposed in a suction tube.
Figure 10:
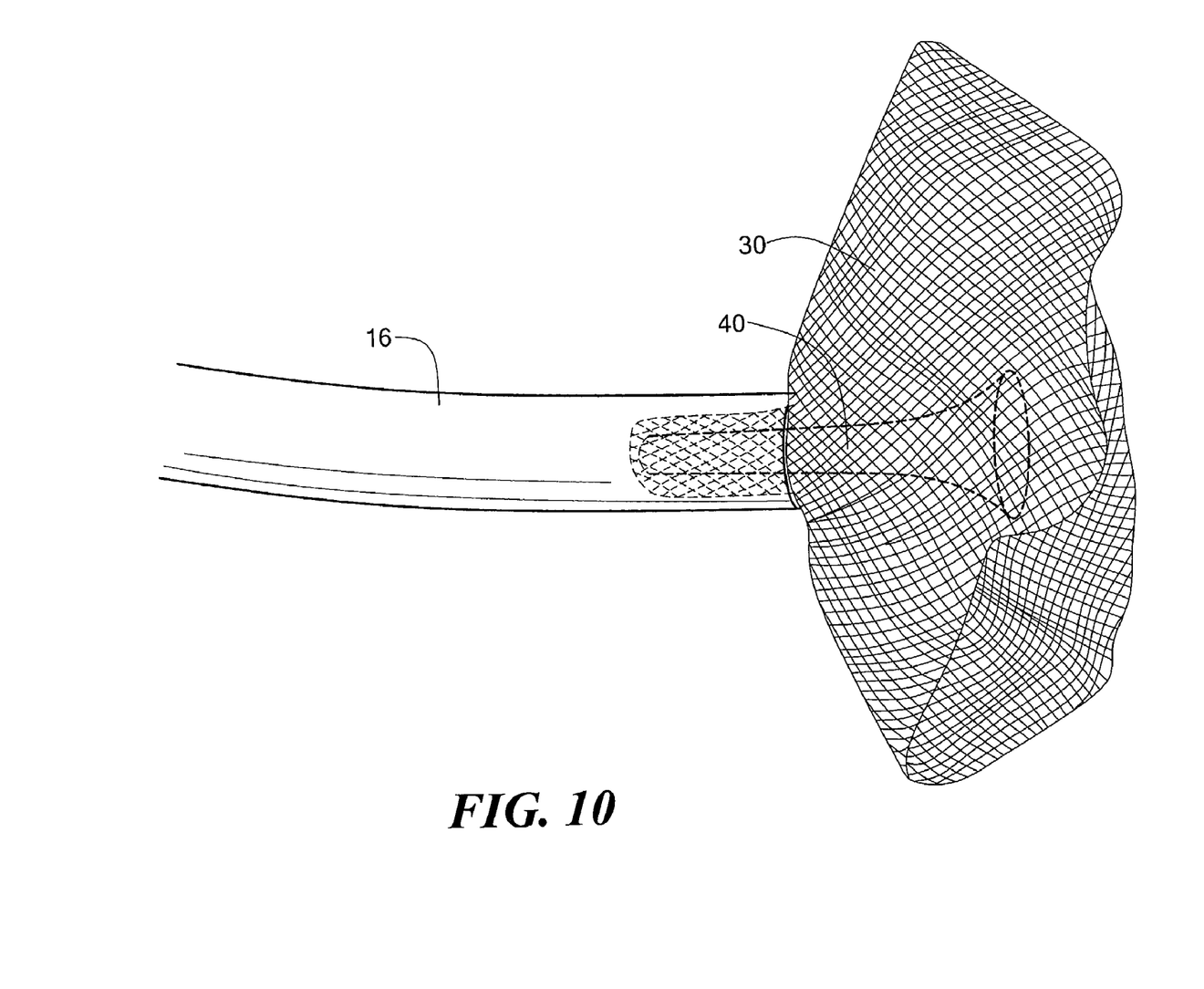
FIG. 10 is another schematic view showing the tissue specimen trap of FIGS. 8 and 9 now disposed in a suction tube.
Figure 11:
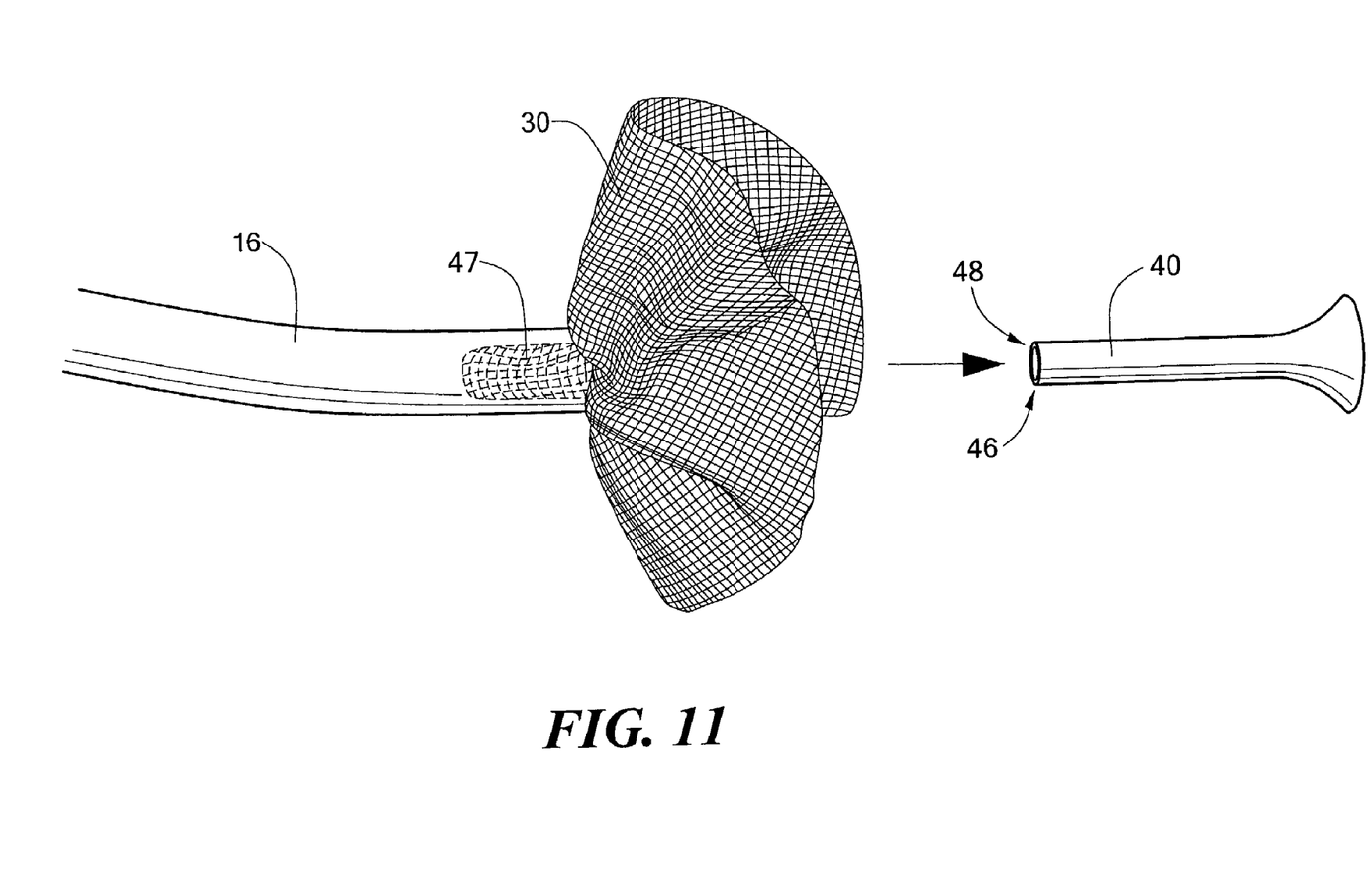
FIG. 11 is a schematic view similar to FIG. 10 with the applicator removed from the suction tube.
Figure 12:
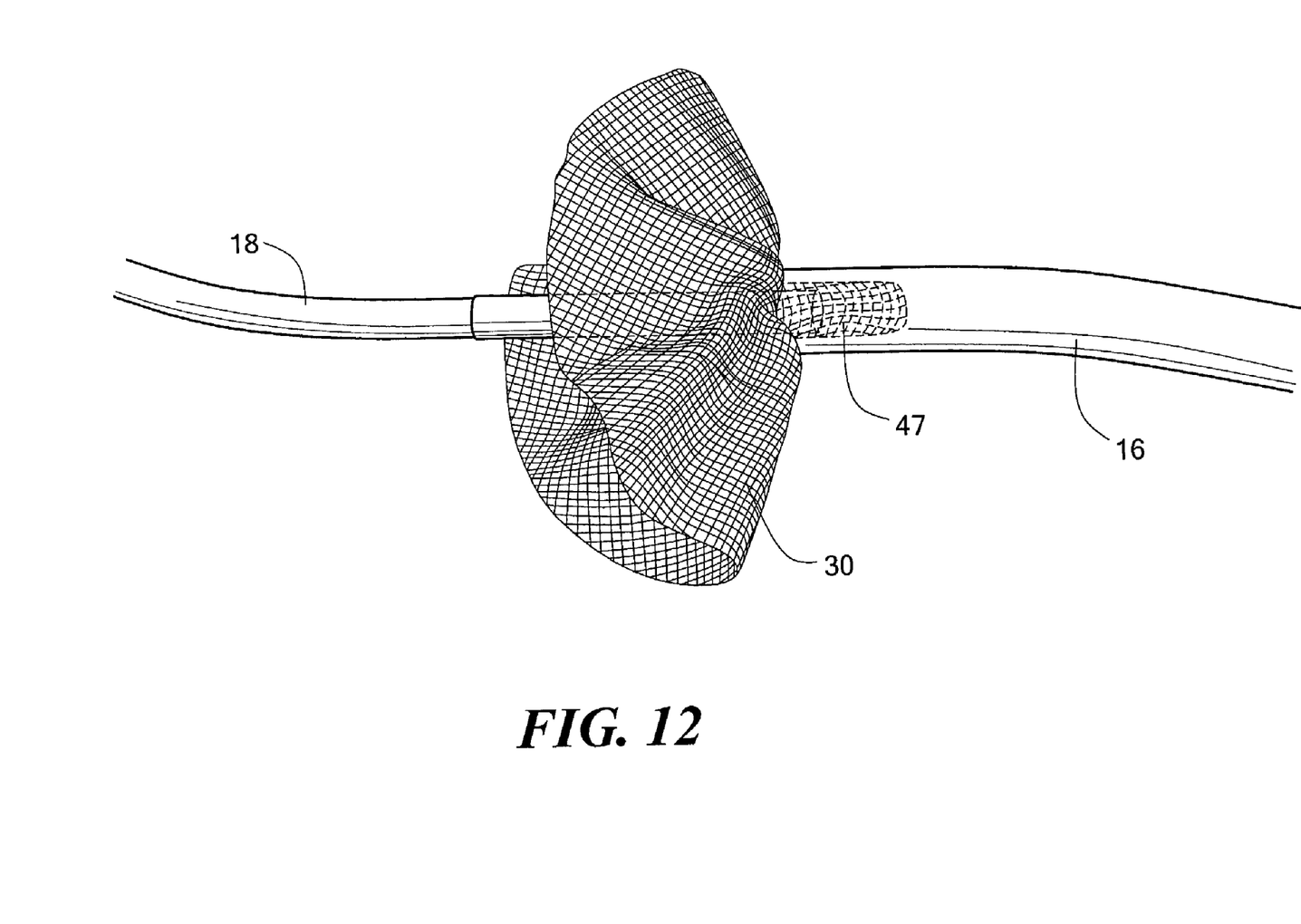
FIG. 12 is a schematic view showing how one end of a second suction tube is connected to the end of the suction tube containing the tissue specimen trap of the subject invention.

In this way, the combination of applicator 40, FIGS. 4–7 and flexible filter 30, FIG. 3 is receivable in suction tube 16, FIGS. 9–10 and configured such that when applicator 40, FIG. 11 is removed, flexible filter 30 forms a removable elongated tissue trap 47 in suction tube 16.

In the preferred embodiment, applicator 40, FIGS. 4–7 is formed to have distal end 42 with an outer diameter of between 0.4 and 0.5 inches, preferably 0.480 inches. The inner diameter of distal end 46 is between 0.1 and 0.2 inches, for example 0.136 inches. The outer diameter of distal end 46 and the outer diameter of shaft 44 in this example is 0.190 inches. Shaft 44 is between 1 and 2 inches in length and in this specific example 1.312 inches in length. Channel 48 is typically between 0.7 and 0.8 inches in length, and in this specific example 0.750 inches deep and 0.136 inches in diameter.

In the preferred embodiment the filter means of this invention is a piece of flexible filter material as shown in FIG. 3 but the invention is not limited to this specific structure for the filter means. Moreover, in the preferred embodiment, the applicator means is applicator 40 shown in FIGS. 4–7 but the subject invention is not limited to this specific applicator for removably inserting the filter means in a suction tube and wherein the applicator means is removable from the suction tube after the filter means is inserted therein. In other designs, channel 48, FIG. 6 need not be enclosed by shaft 44 or there may be no channel at all. In still other designs, the applicator may not be removed from within the suction tube after applying the filter material.

Figure 13:
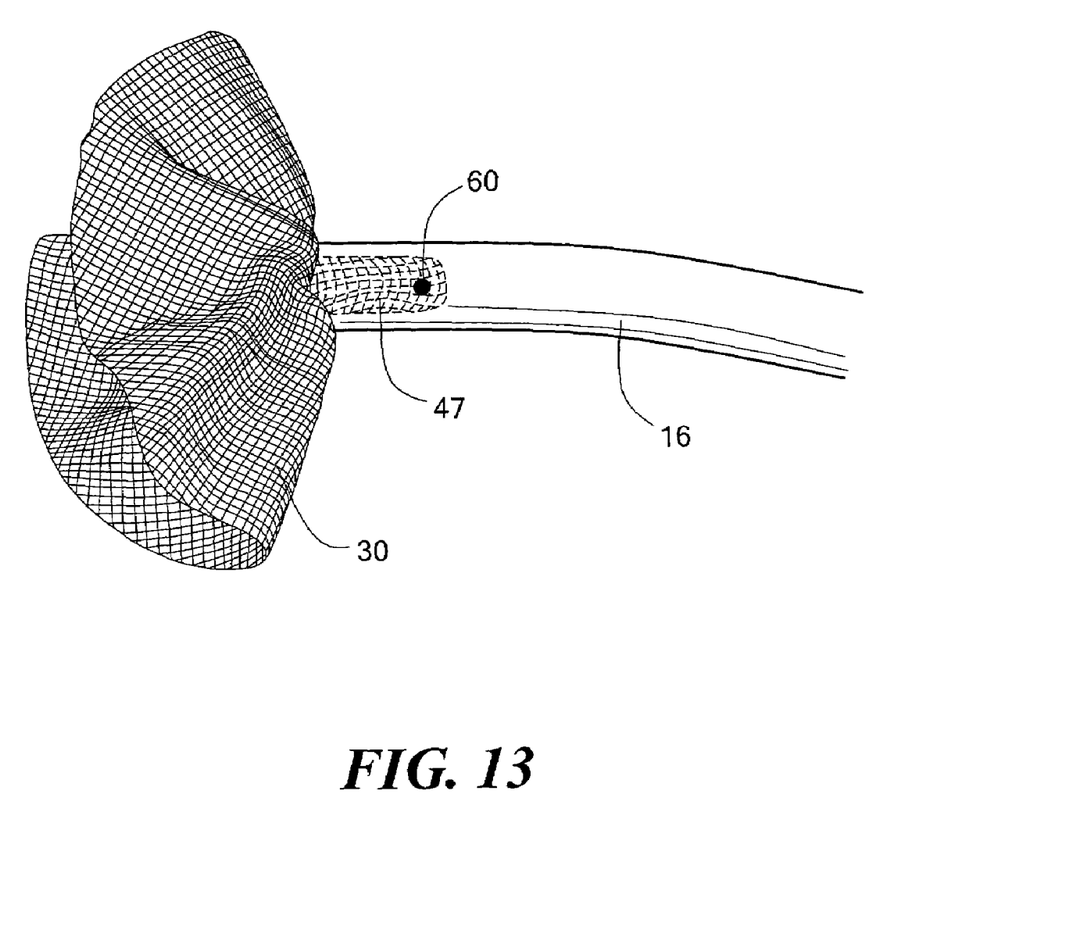
FIG. 13 is a schematic view showing the tissue sample collection trap of the subject invention after a tissue sample has been collected therein and the suction tube leading to the endoscope has been removed therefrom.
Figure 14:
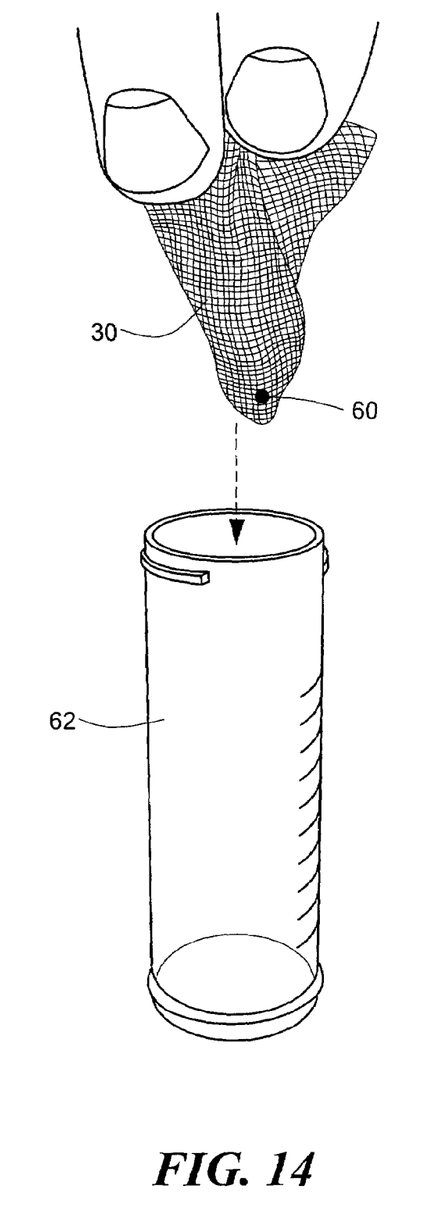
FIGS. 14–15 are schematic views showing how the containerless tissue sample collection trap of the subject invention with a specimen collected therein is transferred into a specimen vial.
Figure 15:
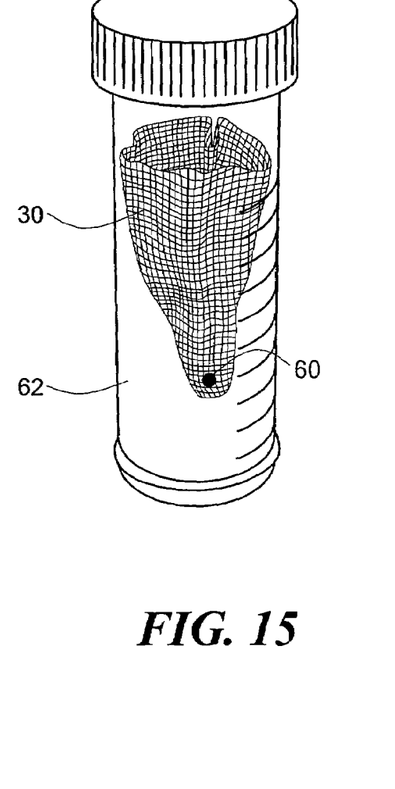
Figure 16:
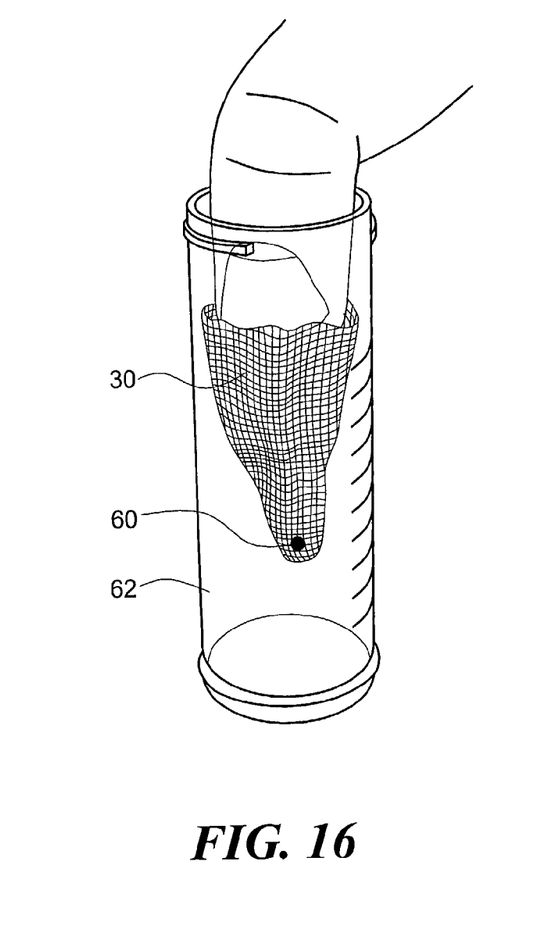
FIG. 16 is a schematic view showing how the pathologist easily removes the containerless tissue sample collection trap of this invention with a tissue sample collected therein from the specimen vial.
Figure 17:
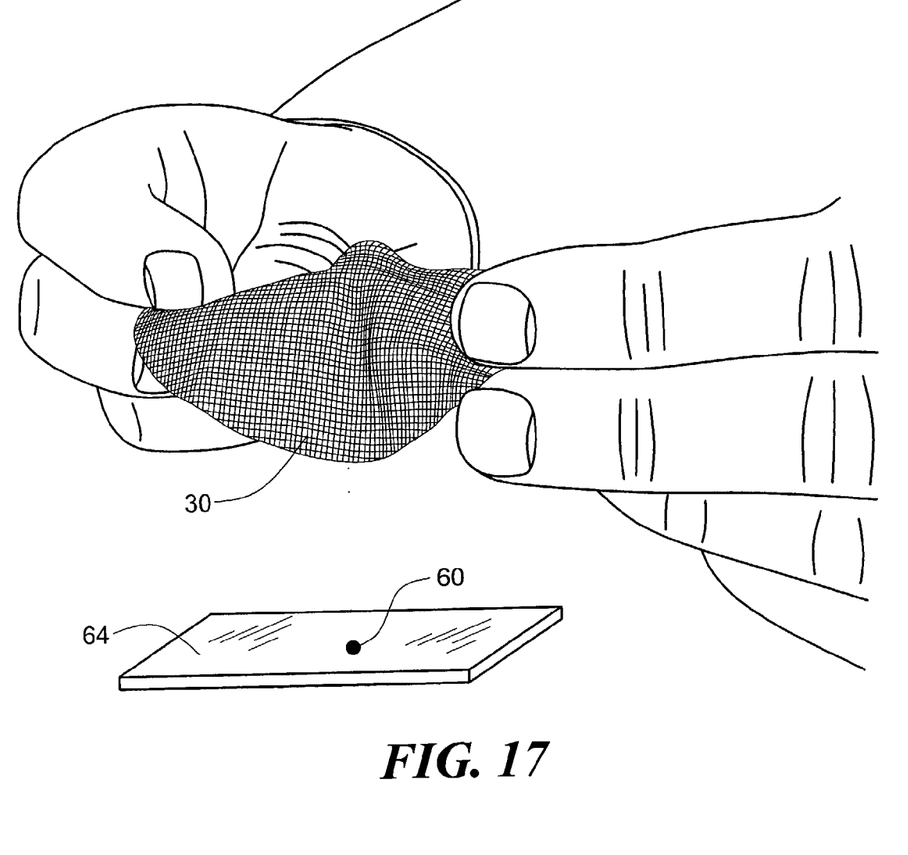
FIG. 17 is a schematic view showing how the pathologist transfers a tissue sample collected within the collection trap of the subject invention to a microscope slide.

FIGS. 8–17 describe the preferred method of trapping tissue wholly within the suction tube or conduit thereby eliminating the need for a prior art tissue specimen trap container in accordance with the subject invention. First, a portion 45, typically the central portion of flexible filter 30, FIG. 3 is loaded into the distal end of applicator 40 as shown in FIG. 8. Typically, the filters are preloaded into the applicators and provided to the hospital in a small box with separate chambers for each tissue collection trap. Then, one end of a suction tube leading to the endoscope is disconnected as shown in FIG. 9 and the distal end of applicator 40 and the flexible filter 30 is urged into that end of the suction tube as shown in FIG. 10. Applicator 40 is then removed as shown in FIG. 11. But, due to friction, the portion of the filter within applicator 40 stays in suction tube 16, as shown, forming trap 47 therein. Elongated tissue trap 47 now resides in suction tube 16. Thus, applicator 40 is used to insert filter 30 into the end of conduit 16 and to form trap 47 therein. Suction tube 16 is then reconnected to suction tube 18, FIG. 12 leading to an endoscope or other surgical apparatus. As shown, a small pocket portion 47 of filter 30 forms a trap within suction tube 16. The surgeon now performs the appropriate procedure and a tissue sample is suctioned through the surgical instrument and travels through suction tube 18 along with fluid to that portion 47 of filter material 30 which resides in suction tube 16. Fluid easily passes through filter material 30 but the tissue specimen 60 can not and is trapped as shown in FIG. 13 after suction tube 18 is removed. Thus, once suction tube 18 is disconnected as shown in FIG. 13, flexible filter 30 and the tissue sample 60 trapped therein is removed from suction tube 16 as shown in FIG. 14 and typically disposed in specimen vial 62, FIG. 15. Specimen vial 62 may be filled with formaldehyde, for example. In the final steps, once specimen vial 62 reaches the pathology lab, the pathologist removes flexible filter 30 and tissue sample 60 trapped therein from specimen vial 62 as shown in FIGS. 16 and 17 and drops tissue specimen 60 onto microscope slide 64, FIG. 17 for examination.

In this way, a containerless tissue sample collection trap apparatus including applicator 40 and netting 30, FIG. 8 can be used in a method of trapping tissue wholly within a suction tube thereby eliminating the need for tissue specimen trap container 20, FIG. 1. The containerless tissue sample collection trap of this invention is small in size thus saving inventory space and inventory and disposal costs. Since tissue is trapped wholly within a suction tube or conduit and since only tissue is trapped, not any fluid, tissue collection is easier and less messy. The containerless tissue sample collection trap of this invention can be manufactured at a much lower cost (e.g., $0.50–1.00) resulting in a cost savings to hospitals and patients. The tissue sample collection trap of this invention itself can be placed directly in specimen vial 62, FIGS. 14–15 for later examination and study. And, the tissue sample collection trap is easy for the pathologist to remove from the specimen vial as shown in FIGS. 16–17.

The tissue trap of this invention traps no fluid and is easier to use because of its containerless design wherein the suction tube itself serves as the tissue collection "container". A filter, preferably a piece of flexible filter material 30, FIG. 3 such as netting is preferably pre-loaded into applicator 40

Figure 4:
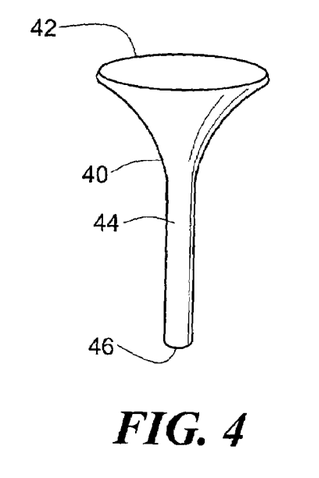
FIG. 4 is a front schematic view of the preferred embodiment of the applicator of the subject invention.
Figure 5:
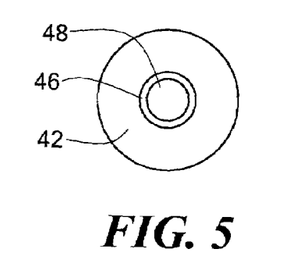
FIG. 5 is a schematic bottom view of the applicator shown in FIG. 4.
Figure 6:
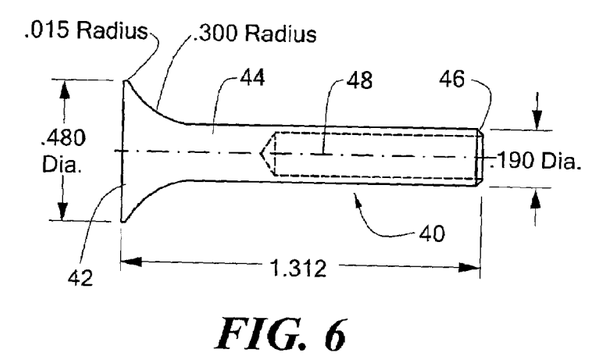
FIG. 6 is a more detailed schematic drawing of the applicator of FIG. 4.
Figure 7:
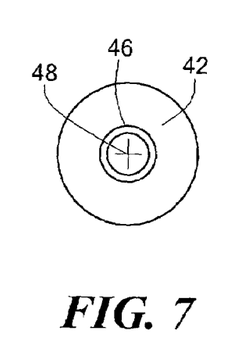
FIG. 7 is a bottom view of the applicator shown in FIG. 6.

FIG. 4 used to dispose the flexible filter within the suction tube as shown in FIGS. 9–11.

Figure 18:
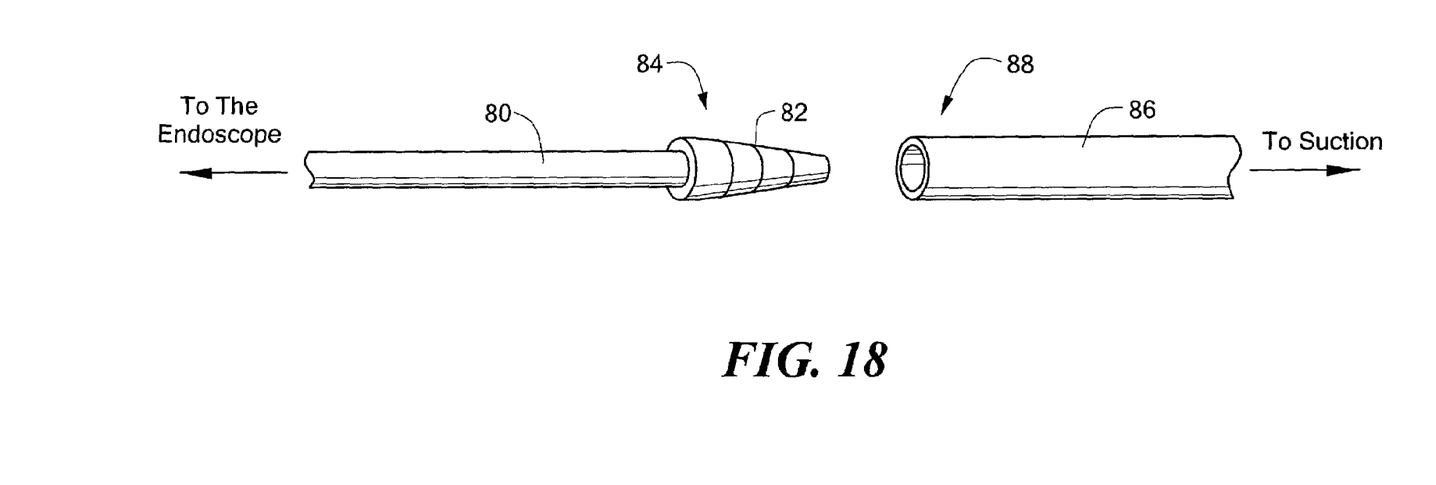
FIGS. 18–21 show the wide versatility of the "containerless" tissue sample collection trap of the subject invention useful with various size suction tube conduits with a variety of different end fittings.

FIGS. 18–21 show the versatility of the "containerless" tissue sample collection trap of the subject invention useful with various size suction tube conduits with a wide variety of different end fittings. In FIG. 18, first conduit 80 is connected to an endoscope and has female fitting 82 on end 84. Second conduit 86 which leads to a suction device has end section 88 with no fitting. A filter, preferably flexible filter 30, FIG. 3 is disposed in end section 88 of conduit 86, FIG. 18 using applicator 40, FIG. 4 or even using female connector 82, FIG. 18 on conduit 80. Because fitting 82 and/or end section 88 of conduit 86 are typically made of plastic and are thus pliable, the netting material of filter 30, FIG. 3 does not cause any fluid leakage when female fitting 82, FIG. 18 is disposed in conduit 86.

Figure 19:
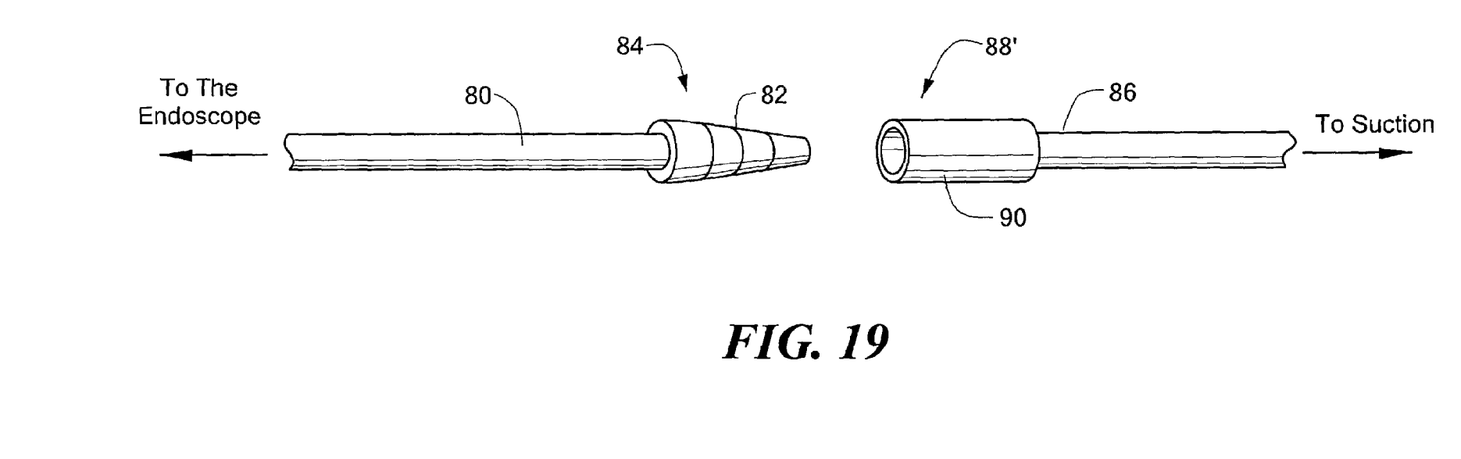
Figure 20:
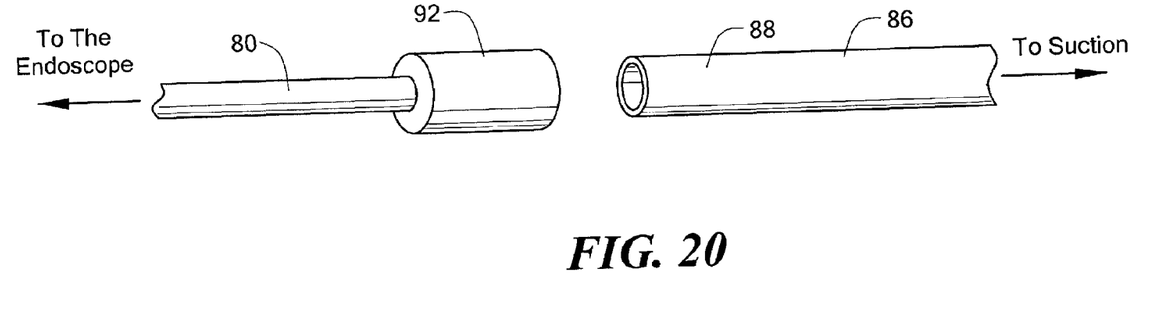
Figure 21:
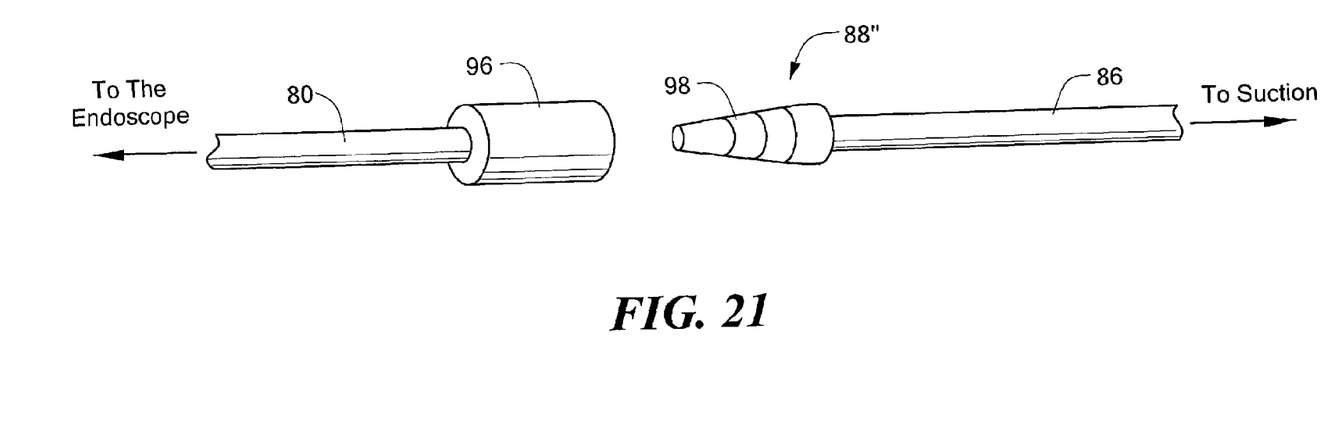

In FIG. 19, end section 88' of conduit 86 includes male fitting 90 which receives the filter and female connection 82 of conduit 84. In FIG. 20, conduit 80 has male fitting 92 received over the end section 88 of conduit 86 which has no fitting. In FIG. 21, the fittings of FIG. 19 are reversed: conduit 80 has male fitting 96 and conduit 86 end section 88" has female fitting 98. Fittings other than the fittings shown in FIGS. 18–21 can be employed and filters other than flexible filter 30, FIG. 3 can be used, however, in accordance with this invention.

Thus, although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims:

What is claimed is:

1. A containerless tissue sample collection trap comprising:
   a flexible netting; and
   an applicator having a shaft terminating in a distal end with a tubular channel therein continuing within said shaft, said channel receiving a portion of the flexible netting, the combination of the applicator and the flexible netting receivable in a suction tube; and
   said applicator and said flexible netting configured such that when the applicator is removed, a pocket in the flexible netting forms a removable elongated tissue trap in the suction tube.

2. The containerless tissue sample collection trap of claim 1 in which the flexible netting is made of a single ply between 2 inches and 5 inches in diameter.

3. The containerless tissue sample collection trap of claim 2 in which the netting is made of a polymer material.

4. The containerless tissue sample collection trap of claim 2 in which the netting has pores between 0.01 and 0.05 inches in perimeter.

5. The containerless tissue sample collection trap of claim 2 in which the netting has between 1,000 and 2,000 pores per square inch.

6. The containerless tissue sample collection trap of claim 1 in which the applicator is made of plastic.

7. The containerless tissue sample collection trap of claim 1 in which the applicator has a broad proximal end opposite the distal end for easier insertion of the distal end thereof into the suction tube.

8. The containerless tissue sample collection trap of claim 7 in which the distal end of the applicator is flat and the channel extends through the flat distal end and continues within the shaft.

9. The containerless tissue sample collection trap of claim 8 in which the outer diameter of the distal end is between 0.4 and 0.5 inches.

10. The containerless tissue sample collection trap of claim 8 in which the inner diameter of the distal end is between 0.1 and 0.2 inches.

11. The containerless tissue sample collection trap of claim 8 in which the shaft is between 1 and 2 inches in length.

12. The containerless tissue sample collection trap of claim 8 in which the channel is between 0.7 and 0.8 inches in length.

13. A containerless tissue sample collection trap comprising:
    a flexible netting; and
    an applicator having a shaft terminating in a distal end and a tubular channel therein extending from the distal end and continuing within said shaft, with a portion of the flexible netting received in the channel, the distal end for urging at least a portion of the flexible netting received in the channel, the distal end for urging at least a portion of the flexible netting into a suction tube, said applicator configured to be removable from said suction tube prior to operation thereof, the combination of the applicator and the flexible netting receivable in a suction tube and configured such that the flexible netting forms a removable elongated tissue trap in the suction tube.

14. A method of trapping tissue wholly within a suction tube thereby eliminating the need for a tissue specimen trap container, the method comprising:
    loading at least a portion of a flexible netting onto an applicator having a tubular channel therein, such that the flexible netting is disposed at least partially within the channel;
    disconnecting one end of a suction tube;
    urging the applicator and the flexible netting filter into the disconnected end of the suction tube;
    optionally removing the applicator; and
    reconnecting the end of the suction tube.

15. The method of claim 14 further including the step of disconnecting the suction tube and removing the flexible netting and a tissue sample trapped therein from the suction tube.

16. The method of claim 14 further including the step of placing the flexible netting and the tissue sample trapped therein in a specimen vial.

17. The method of claim 16 further including the step of removing the flexible netting and the tissue sample trapped therein from the specimen vial.

18. The method of claim 17 further including the step of removing the tissue sample from the flexible netting for examination.

19. The method of claim 14 in which the flexible netting is made of a single ply of netting between 2 and 5 inches in diameter.

20. The method of claim 19 in which the netting is made of a polymer material.

21. The method of claim 19 in which the netting has pores between 0.01 and 0.05 inches in perimeter.

22. The method of claim 19 in which the netting has between 1,000 and 2,000 pores per square inch.

23. The method of claim 14 in which the applicator is made of plastic.

24. The method of claim 14 in which the applicator has a broad proximal end opposite the distal end for easier insertion of the distal end thereof into the suction tube.

25. The method of claim 14 in which the distal end of the applicator is flat and the channel extends through from flat distal end.

26. The method of claim 25 in which the outer diameter of the distal end is between 0.4 and 0.5 inches.

27. The method of claim 25 in which the inner diameter of the distal end is between 0.1 and 0.2 inches.

28. A method of making a containerless tissue trap, the method comprising:
    forming an applicator with a shaft terminating in a distal end with a tubular channel therein and continuing within said shaft; and
    inserting a portion of a flexible netting into the channel, the combination of the applicator and the flexible netting receivable in a suction tube and configured such that when the applicator is removed, a pocket in the flexible netting forms a removable elongated tissue trap in the suction tube.

29. A containerless tissue sample collection trap comprising:
    a first conduit having a fitting on one end thereof;
    a second conduit having an end section connectable to the fitting of the first conduit, the fitting received in the end section of the second conduit forming a junction between the two conduits;
    the fitting and/or the end section of the second conduit being pliable to join the two conduits; and
    a flexible netting removably disposed in the end section of the second conduit such that when the first conduit is joined to the second conduit tissue is trapped in the end section of the second conduit.

30. The containerless tissue sample collection trap of claim 29 in which the end section of the second conduit also includes a fitting and the flexible netting is disposed in the fitting.

31. The containerless tissue sample collection trap of claim 30 in which said first conduit fitting is a male fitting.

32. The containerless tissue sample collection trap of claim 30 in which said first conduit fitting is a female fitting.

33. The containerless tissue sample collection trap of claim 29 in which said flexible netting forms an elongated tissue trap in the second conduit and flexible netting material extends out of the joint between the two conduits.

34. The containerless tissue sample collection trap of claim 29 further including an applicator for disposing the flexible netting in the end section of the second conduit.

35. A containerless tissue sample collection trap comprising:
    a flexible netting; and
    an applicator having a shaft terminating in a distal end and a tubular channel therein extending from the distal end and continuing within said shaft, with a portion of the flexible netting received in the channel, the distal end for urging at least a portion of the flexible netting received in the channel, the distal end for urging at least a portion of the flexible netting into a suction tube, said applicator configured to be removable from said suction tube prior to operation thereof, the combination of the applicator and the flexible netting receivable in a suction tube and configured such that the flexible netting forms a removable elongated tissue trap in the suction tube.

36. The containerless tissue sample collection trap of claim 35 in which the distal end of the applicator is flat and the channel extends through the flat distal end and continues within the shaft.

37. The containerless tissue sample collection trap of claim 36 in which the outer diameter of the distal end is between 0.4 and 0.5 inches.

38. The containerless tissue sample collection trap of claim 36 in which the inner diameter of the distal end is between 0.1 and 0.2 inches.

39. The containerless tissue sample collection trap of claim 36 in which the shaft is between 1 and 2 inches in length.

40. The containerless tissue sample collection trap of claim 36 in which the channel is between 0.7 and 0.8 inches in length.

41. A containerless tissue sample collection trap comprising:
    a first conduit having a female fitting on one end thereof;
    a second conduit having an end section including a male fitting connectable to the fitting of the first conduit forming a junction between the two conduits;
    the male fitting and/or the end section of the second conduit being pliable to join the two conduits, the female fitting received in the end section of the section conduit; and
    a flexible netting removably disposed in the end section male fitting of the second conduit such that when the first conduit is joined to the second conduit tissue is trapped in the end section of the second conduit.

42. A containerless tissue sample collection trap comprising:
    a first conduit having a fitting on one end thereof;
    a second conduit having an end section connectable to the fitting of the first conduit forming a junction between the two conduits;
    the fitting and/or the end section of the second conduit being pliable to join the two conduits; and
    a flexible netting removably disposed in the end section of the second conduit such that when the first conduit is joined to the second conduit tissue is trapped in the end section of the second conduit, said flexible netting forming an elongated tissue trap in the second conduit and having said flexible netting material extending out of the joint between the two conduits.

43. A containerless tissue sample collection trap comprising:
    a flexible filter; and
    an applicator having a shaft terminating in a distal end for urging at least a portion of the flexible filter into a suction tube and a tubular channel therein extending from the distal end thereof and continuing within said shaft, and a portion of the flexible filter is received therein, the combination of the applicator and the flexible filter receivable in a suction tube and configured such that the flexible filter forms a removable elongated tissue trap in the suction tube.

44. A containerless tissue sample collection trap comprising:
    a first conduit having a female fitting on one end thereof;
    a second conduit having an end section connectable to the female fitting of the first conduit, the female fitting received in the end section of the second conduit forming a junction between the two conduits, the end section of the second conduit being pliable to join the two conduits; and a flexible netting removably disposed in the male fitting and/or end section of the second conduit such that when the first conduit is joined to the second conduit tissue is trapped in the end section of the second conduit.

45. A containerless tissue sample collection trap comprising:
a first conduit having a female fitting on one end thereof;
a second conduit having an end section connectable to the fitting of the first conduit, the fitting received in the end section of the second conduit forming a junction between the two conduits; the fitting and/or the end section of the second conduit being pliable to join the two conduits;
a flexible netting removably disposed in the end section of the second conduit such that when the first conduit is joined to the second conduit tissue is trapped in the end section of the second conduit; and
an applicator separate from said conduits for disposing the filter in the end section of the second conduit.

* * * * *